(12) United States Patent
Lewis et al.

(10) Patent No.: US 11,906,500 B1
(45) Date of Patent: Feb. 20, 2024

(54) APPARATUS FOR MEASURING FUEL THERMAL STABILITY, DEPOSIT FORMATION RATE, AND IN-SITU REACTIVITY VIA OPTICAL METHODS

(71) Applicant: Government of the United States, as represented by the Secretary of the Air Force, Wright-Patterson AFB, OH (US)

(72) Inventors: William K. Lewis, Dayton, OH (US); Elizabeth M Craft, Dayton, OH (US); Patrick S Walsh, Dayton, OH (US)

(73) Assignee: The Government of the United States of America as Represented by the Secretary of the Air Force, Wright-Patterson AFB, OH (US)

( * ) Notice: Subject to any disclaimer, the term of this patent is extended or adjusted under 35 U.S.C. 154(b) by 761 days.

(21) Appl. No.: 17/034,243

(22) Filed: Sep. 28, 2020

(51) Int. Cl.
*G01N 33/28* (2006.01)
*G01N 15/06* (2006.01)

(52) U.S. Cl.
CPC ..... *G01N 33/2805* (2013.01); *G01N 15/0612* (2013.01)

(58) Field of Classification Search
CPC .................. G01N 33/2805; G01N 15/0612
See application file for complete search history.

(56) References Cited

U.S. PATENT DOCUMENTS

| | | | | |
|---|---|---|---|---|
| 3,529,464 A | * | 9/1970 | Lander, Jr. | G01N 33/2805 73/61.62 |
| 3,670,561 A | * | 6/1972 | Hundere | G01N 33/2805 73/61.62 |
| 4,135,881 A | * | 1/1979 | Bakx | G01N 33/2805 422/89 |
| 5,198,871 A | | 3/1993 | Hill, Jr. et al. | |
| 5,223,718 A | | 6/1993 | Taboada | |
| 5,293,218 A | * | 3/1994 | Morris | G01B 11/0675 356/627 |
| 5,348,645 A | | 9/1994 | Maggard et al. | |
| 5,370,790 A | | 12/1994 | Maggard et al. | |
| 5,712,481 A | | 1/1998 | Welch et al. | |
| 7,297,963 B2 | | 11/2007 | Moses et al. | |
| 8,262,283 B2 | * | 9/2012 | Yang | G01N 33/2805 374/45 |

* cited by examiner

*Primary Examiner* — Roy M Punnoose
(74) *Attorney, Agent, or Firm* — AFMCLO/JAZ; James F. McBride

(57) ABSTRACT

The present invention relates to apparatus for measuring fuel thermal stability, deposit formation rate, and in-situ reactivity via optical methods and as well as methods of making and using same. Applicants' apparatus can deliver the rate and amount of degradation as well as the quantifying and qualifying the chemical species in the fuel on a real time basis during a test. As a result, Applicants' apparatus provides significantly improved performance over the current apparatuses.

21 Claims, 3 Drawing Sheets

APPARATUS FOR MEASURING FUEL THERMAL STABILITY, DEPOSIT FORMATION RATE, AND IN-SITU REACTIVITY VIA OPTICAL METHODS

RIGHTS OF THE GOVERNMENT

The invention described herein may be manufactured and used by or for the Government of the United States for all governmental purposes without the payment of any royalty.

FIELD OF THE INVENTION

The present invention relates to apparatus for measuring fuel thermal stability, deposit formation rate, and in-situ reactivity via optical methods and as well as methods of making and using same.

BACKGROUND OF THE INVENTION

Current apparatuses for fuel thermal stability testing exist but such apparatuses cannot measure the fuel thermal stability when the fuel's temperature exceeds 400° C. and such apparatuses are inefficient when measuring fuel thermal stability when the fuel's temperature exceeds 275° C. as the reproducibility of the test suffers. Furthermore, current apparatuses are inefficient as they are slow, as they take several hours to deliver results and cannot quantify and qualify the chemical species in the subject fuel in real time.

Applicants recognized that the source of the aforementioned problems was that current apparatuses did not employ an optical access, and even more importantly an optical access that is suitable for use at fuel temperatures in excess of 400° C. Applicants discovered that by having the correct optical access, the rate of fuel degradation can be determined in real time. Thus, for purposes of the present application, the fuel's thermal stability can be determined in real time as the aforementioned degradation and thermal stability become one and the same when the correct optical access is employed. Furthermore, unlike current apparatuses, Applicants' apparatus can deliver the rate and amount of degradation as well as the quantifying and qualifying chemical species in the fuel on a real time basis during a test. As a result, Applicants' apparatus provides significantly improved performance over the current apparatuses.

SUMMARY

The present invention relates to apparatus for measuring fuel thermal stability, deposit formation rate, and in-situ reactivity via optical methods and as well as methods of making and using same. Applicants' apparatus can deliver the rate and amount of degradation as well as the quantifying and qualifying the chemical species in the fuel on a real time basis during a test. As a result, Applicants' apparatus provides significantly improved performance over the current apparatuses.

BRIEF DESCRIPTION OF THE DRAWINGS

The accompanying drawings, which are incorporated in and constitute a part of this specification, illustrate embodiments of the present invention and, together with a general description of the invention given above, and the detailed description of the embodiments given below, serve to explain the principles of the present invention.

Figure 1:
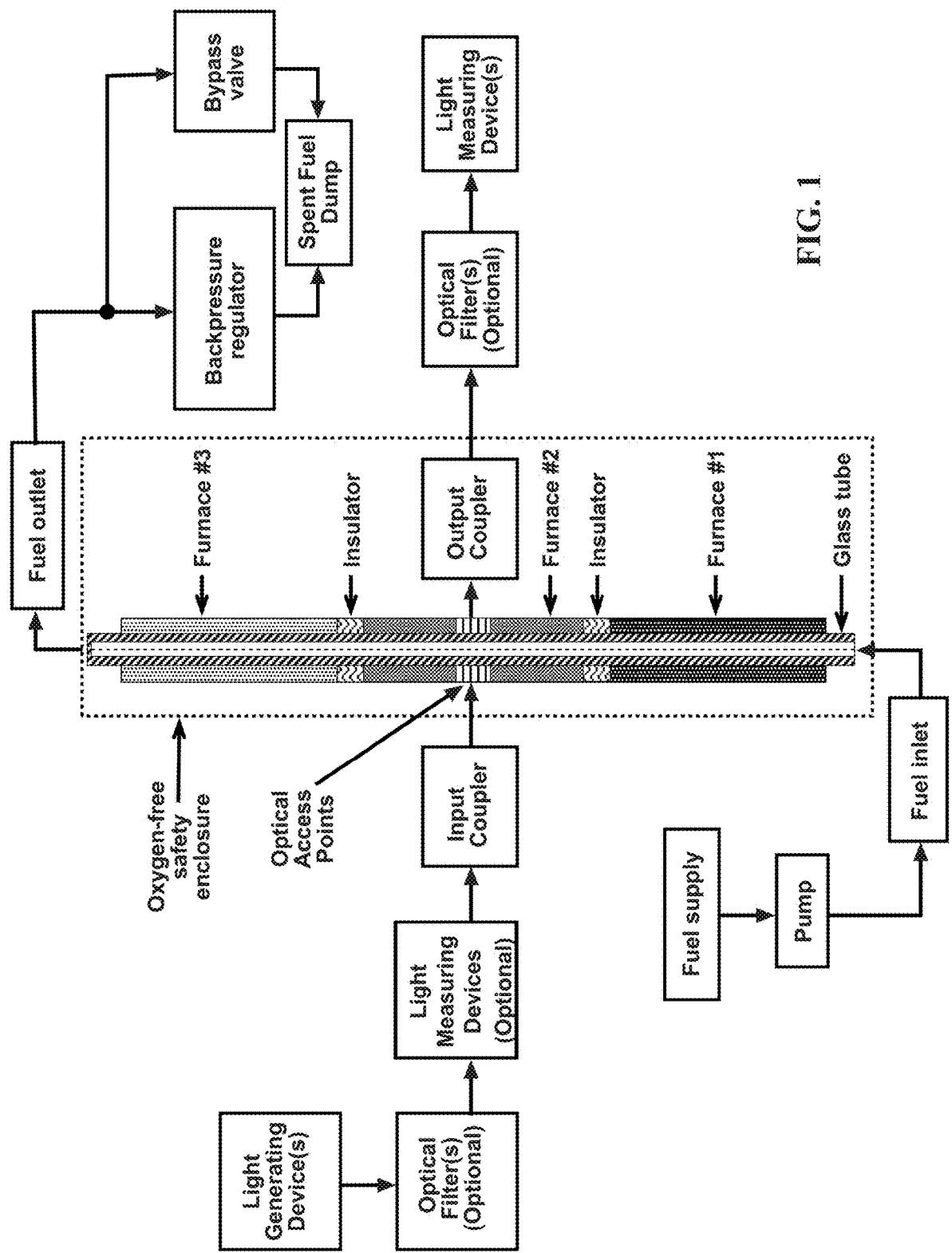
FIG. 1 shows an embodiment of the invention in which optical access to the fuel flow is provided using a glass tube to enclose the flowing fuel as it is heated.

It should be understood that the appended drawings are not necessarily to scale, presenting a somewhat simplified representation of various features illustrative of the basic principles of the invention. The specific design features of the sequence of operations as disclosed herein, including, for example, specific dimensions, orientations, locations, and shapes of various illustrated components, will be determined in part by the particular intended application and use environment. Certain features of the illustrated embodiments have been enlarged or distorted relative to others to facilitate visualization and clear understanding. In particular, thin features may be thickened, for example, for clarity or illustration.

DETAILED DESCRIPTION OF THE INVENTION

Definitions

Unless specifically stated otherwise, as used herein, the terms "a", "an" and "the" mean "at least one".

As used herein, the terms "include", "includes" and "including" are meant to be non-limiting.

Unless otherwise noted, all component or composition levels are in reference to the active portion of that component or composition, and are exclusive of impurities, for example, residual solvents or by-products, which may be present in commercially available sources of such components or compositions.

All percentages and ratios are calculated by weight unless otherwise indicated. All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Apparatus for Measuring Fuel Thermal Stability, Deposit Formation Rate, and In-Situ Reactivity Applicants disclose an apparatus comprising:
a) a chamber, said chamber having an inlet, and an outlet
b) one or more areas of said apparatus providing optical access to said chamber, said one or more areas being configured to deliver and collect light via fiber optics and/or free space couplings;
c) one or more heat sources capable of heating one or more areas of said chamber;
d) one or more devices for providing a pressure differential between said chamber's inlet and said chamber's outlet, said one or more devices being located in communication with said chamber's inlet or said chamber's outlet with the proviso that when said apparatus comprises two or more of said devices, said devices may be located in communication with said chamber's inlet and/or said chamber's outlet; preferably said apparatus comprises one device providing a pressure differential between said chamber's inlet and said chamber's outlet, said device being located in communication with said chamber's inlet;

e) one or more devices for controlling the absolute pressure in said chamber, said one or more devices being located in communication with said chamber's inlet or said chamber's outlet with the proviso that when said apparatus comprises two or more of said devices, said devices may be located in communication with said chamber's inlet and/or said chamber's outlet, said one or more devices when in communication with said chamber's inlet being located before or after said any of said one or more devices for providing a pressure differential between said chamber's inlet and said chamber's outlet that are in communication with said chamber's inlet; preferably said apparatus comprises one device for controlling the absolute pressure in said chamber, said device being located in communication with said chamber's outlet;

f) one or more devices for providing light to said one or more areas of optical access to said chamber;

g) one or more devices for collecting light from said one or more areas of optical access to said chamber;

h) one or more devices for measuring one or more properties of said collected light and optionally one or more devices for one or more properties of said provided light and/or one or more devices for measuring one or more properties of said collected light and optionally one or more properties of said provided light; and i) optionally, one or more optical filters for filtering light, said one or more optical filters for filtering light being placed before and/or incorporated into said one or more devices for providing light to said one or more areas of optical access to said chamber, before and/or incorporated into said one or more devices for collecting light from said one or more areas of optical access to said chamber and/or before and/or incorporated into said one or more devices for measuring one or more properties of said collected light and optionally one or more properties of said provided light. As will be appreciated by the skilled artisan, the chamber recited herein may include one or more windows and/or complete sections that provide the optical access recited herein.

Applicants disclose the apparatus according to Paragraph 0017 wherein:

a) said chamber has a symmetric shape or an asymmetric shape, preferably said chamber is cylindrical, rectangular, spherical, or cubic, more preferably said chamber is cylindrical or rectangular, more preferably said chamber is cylindrical or rectangular, most preferably said chamber is cylindrical;

b) said apparatus comprises three or more heat sources capable of heating three or more areas of said chamber, preferably said apparatus comprises three or more heat sources capable of isothermally heating three or more areas of said chamber, more preferably said apparatus comprises three or more heat sources capable of isothermally heating three or more areas of said chamber with thermal insulation between each isothermal heated zone;

c) said apparatus comprises two or more areas of optical access to said chamber, preferably said apparatus comprises two or more areas of optical access to said chamber for each of said at least one heat source, more preferably said apparatus comprises three or more areas of optical access to said chamber for each of said at least one heat source;

d) said one or more devices for providing a pressure differential between said chamber's inlet and said chamber's outlet comprises a pump and/or pressurized vessel providing a pressure differential between said chamber's inlet and said chamber's outlet; preferably said one or more devices for providing a pressure differential between said chamber's inlet and said chamber's outlet comprises a pump providing a pressure differential between said chamber's inlet and said chamber's outlet;

e) said one or more devices for controlling the absolute pressure in said chamber comprises one or more pressure or flow regulator devices located either upstream or downstream of said at least one heat source, preferably said one or more devices for controlling the absolute pressure in said chamber comprises a pressure regulator device for controlling the absolute pressure in said chamber, more preferably said one or more devices for controlling the absolute pressure in said chamber comprises a pressure regulator located upstream of said at least one heat source or a backpressure regulator located downstream of said at least one heat source, most preferably said one or more devices for controlling the absolute pressure in said chamber comprises a backpressure regulator located downstream of said at least one heat source;

f) each of said one or more devices for providing light to said one or more areas of optical access to said chamber is independently a laser, a lamp, a light emitting diode or a glow bar, preferably each of said one or more devices for providing light to said one or more areas of optical access to said chamber is independently a laser or a light emitting diode, more preferably each of said one or more devices for providing light to said one or more areas of optical access to said chamber is independently a laser or a light emitting diode having an emission spectrum of from about 9.99 nm to about 0.01 nm in breadth, most preferably each of said one or more devices for providing light to said one or more areas of optical access to said chamber is independently a laser or a light emitting diode having an emission spectrum of from about 1.99 nm to about 0.01 nm in breadth;

g) each of said one or more devices for collecting light from said one or more areas of optical access to said chamber comprises a fiber optic device or a free space coupled device, preferably each of said one or more devices for collecting light from said one or more areas of optical access to said chamber comprises a fiber optic device, more preferably each of said one or more devices for collecting light from said one or more areas of optical access to said chamber comprises a fiber optic device having temperature tolerance above about 200° C. to about 1700° C., most preferably each of said one or more devices for collecting light from said one or more areas of optical access to said chamber comprises a fiber optic device having temperature tolerance above about 700° C. to about 1700° C.;

h) each of said one or more devices for measuring one or more properties of said collected light and optionally one or more properties of said provided light is independently a spectrometer, a monochromator, a spectrum analyzer, a photodiode, a photomultiplier tube, an avalanche detector, a camera, a charge coupled device array, a complementary metal oxide semiconductor detector, a photoreceiver, or a polarimeter, preferably each of said one or more devices for measuring one or more properties of said collected light and optionally one or more properties of said provided light is independently a spectrometer, a monochromator, a spectrum analyzer, a photodiode, a photomultiplier tube, an avalanche detector, a camera, a charge coupled device array, a complementary metal oxide semiconductor detector or a photoreceiver, more preferably each of said one or more devices for measuring one or more properties of said collected light and optionally one or more properties of said provided light is independently a spectrometer, a photodiode, or a photoreceiver, most preferably each of said one or more devices for measuring one or more properties of said collected light and optionally one or more properties of said provided light is independently a spectrometer or a photodiode.

Applicants disclose the apparatus according to Paragraphs 0017 through 0018 wherein:
  a) said chamber comprises a material selected from the group coinciding of steel, iron, brass, bronze, copper, titanium, tantalum, nickel, tungsten, silver, gold, platinum, aluminum, glass, quartz, sapphire, silicon dioxide, diamond, rubber, plastic, graphite and mixtures thereof, preferably said chamber comprises a material selected from the group coinciding of steel, brass, copper, aluminum, quartz, sapphire, glass, rubber and graphite and mixtures thereof, more preferably said chamber comprises a material selected from the group coinciding of steel, brass, copper, quartz, sapphire, rubber and graphite and mixtures thereof, most preferably said chamber comprises a material selected from the group coinciding of steel, quartz, graphite and mixtures thereof,
  b) each of said one or more areas of said apparatus providing optical access to said chamber independently comprising a material selected from the group consisting of glass, quartz, sapphire, silicon dioxide, diamond, zirconium fluoride, indium fluoride, magnesium fluoride, calcium fluoride, silicon, barium fluoride, zinc selenide, germanium, zinc sulfide, and mixtures thereof, preferably each of said one or more areas of said apparatus providing optical access to said chamber comprising a material selected from the group consisting of glass, quartz, sapphire, silicon dioxide, zirconium fluoride, indium fluoride, magnesium fluoride, calcium fluoride, silicon, barium fluoride, zinc selenide, germanium, zinc sulfide, and mixtures thereof, more preferably each of said one or more areas of said apparatus providing optical access to said chamber comprising a material selected from the group consisting of glass, quartz, silicon dioxide, zirconium fluoride, indium fluoride, magnesium fluoride, calcium fluoride, silicon, barium fluoride, zinc selenide, and mixtures thereof;
  c) each of said heat sources capable of heating one or more areas of said chamber is independently selected from the group consisting of resistive heaters, laser heating, electron beam heating, convective ovens, and radiative heaters, preferably each of said heat sources capable of heating one or more areas of said chamber is independently selected from the group consisting of resistive heaters, convective ovens, and radiative heaters, more preferably each of said heat sources capable of heating one or more areas of said chamber is independently selected from the group consisting of resistive heaters and radiative heaters, most preferably each of said heat sources capable of heating one or more areas of said chamber is independently selected from the group consisting of resistive heaters.

Applicants disclose the apparatus according to Paragraphs 0017 through 0019 wherein at least one of said devices for measuring one or more properties of said collected light measures one or more properties of said provided light.

Method of Use

Applicants disclose a method of determining the thermal stability of a hydrocarbon, said method comprising passing said hydrocarbon through the apparatus of Paragraphs 0017 through 0020.

Applicants disclose the method of Paragraph 0021 wherein said hydrocarbon is a fuel, preferably said fuel is a rocket, jet, or missile fuel, more preferably said fuel is kerosene based, most preferably said fuel is selected from the group consisting of JP7, JP10, JP8, JP5, JetA, JetA1, F24, RP2 and mixtures thereof.

Applicants disclose the method of Paragraphs 0021 through 0022 wherein:
  a) said hydrocarbon is heated while in said apparatus's chamber to a temperature of from about 150° C. to 750° C. about, preferably said hydrocarbon is heated while in said apparatus's chamber to a temperature of from about 200° C. to 750° C. about, more preferably said hydrocarbon is heated while in said apparatus's chamber to a temperature of from about 400° C. to 750° C. about, most preferably said hydrocarbon is heated while in said apparatus's chamber to a temperature of from about 500° C. to 750° C. about; preferably when said hydrocarbon is heated, said hydrocarbon is heated at a rate of from about 2.5° C./sec. to about 7500° C./sec, or said hydrocarbon is heated, said hydrocarbon is heated at a rate of from about 75° C./sec. to about 750° C./sec.;
  b) said hydrocarbon having a residence time in said chamber from about 0.1 seconds to about 300 seconds, preferably said hydrocarbon having a residence time in said chamber from about 0.1 seconds to about 100 seconds, more preferably said hydrocarbon having a residence time in said chamber from about 0.1 seconds to about 10 seconds;
  c) the absolute pressure in said chamber is from about 1 atm to about 200 atm; in one aspect the absolute pressure in said chamber is from about 3 atm to about 150 atm, in another aspect the absolute pressure in said chamber is from about atm to about 150 atm, in another aspect the absolute pressure in said chamber is from about 25 atm to about 150 atm;
  d) light is provided to one or more areas of optical access to said chamber;
  e) light is collected from said one or more areas of optical access to said chamber; and
  f) said collected light is measured, and said provided light is optionally measured, preferably said provided light is measured prior to being provided.

Applicants disclose the method of Paragraphs 0021 through 0023 wherein said provided light is measured.

Applicants disclose the method of Paragraphs 0021 through 0024 wherein:
  a) said provided light has a wavelength of from about 180 nm to about 20 µm, preferably said provided light has a wavelength of from about 400 nm to about 4 µm, more preferably said provided light has a wavelength of from about 400 to about 700 nm, most preferably said provided light has a wavelength of from about 400 nm to about 450 nm; and/or b) said collected light has a wavelength of from about 180 nm to about 20 μm, preferably said provided light has a wavelength of from about 400 nm to about 4 μm, more preferably said provided light has a wavelength of from about 400 to about 700 nm, most preferably said provided light has a wavelength of from about 400 nm to about 600 nm; and the wavelength of said provided light is filtered out of said collected light.

Applicants disclose the method of Paragraphs 0021 through 0025 wherein said method comprises one, two, three or four of the following steps:

a) said provided light is provided by a laser, a lamp, a light emitting diode, and/or a glow bar; preferably said provided light is provided by a laser and/or a light emitting diode; more preferably said provided light is provided by a laser and/or a light emitting diode having an emission spectrum from about 9.99 nm to about 0.01 nm in breath; most preferably said provided light is provided by a laser and/or a light emitting diode, said light emitting diode having an emission spectrum from about 1.99 nm to about 0.01 nm in breath;

b) said provided light is measured by a spectrometer, a monochromator, a spectrum analyzer, a photodiode, a photomultiplier tube, an avalanche detector, a camera, a charge coupled device array, a complementary metal oxide semiconductor detector, a photoreceiver, and/or a polarimeter; preferably said provided light is measured by a spectrometer, a monochromator, a spectrum analyzer, photodiode, a photomultiplier tube, an avalanche detector, a camera, a charge coupled device array, a complementary metal oxide semiconductor detector, and/or a photoreceiver; more preferably said provided light is measured by a spectrometer, a photodiode, and/or a photoreceiver; most preferably said provided light is measured by a photodiode and/or a photoreceiver;

c) said collected light is collected by a fiber optic device and/or free space coupled device; preferably said collected light is collected by a fiber optic device; more preferably said collected light is collected by a fiber optic device having temperature tolerance above about 200° C. to about 1700° C.; most preferably said collected light is collected by a fiber optic devices having temperature tolerance above about 700° C. to about 1700° C.;

d) said collected light is measured by a spectrometer, a monochromator, spectrum analyzer, a photodiode, a photomultiplier tube, an avalanche detector, a camera, a charge coupled device array, a complementary metal oxide semiconductor detector, a photoreceiver, and/or a polarimeter;

preferably said collected light is measured by a spectrometer, a monochromator, a spectrum analyzer, a photodiode, a photomultiplier tube, an avalanche detector, a camera, a charge coupled device array, a complementary metal oxide semiconductor detector, and/or a photoreceiver; more preferably said collected light is measured by a spectrometer, a photodiode, and/or a photoreceiver; most preferably said collected light is measured by a spectrometer and/or a photodiode.

Applicants disclose the method of Paragraphs 0021 through 0026 wherein the collected light and/or provided light is analyzed for at least one of the following properties wavelength, intensity, Raman shift, polarity, and phase, preferably the collected light and/or provided light is analyzed for at least one of the following properties wavelength, intensity, Raman shift and polarity, more preferably the collected light and/or provided light is analyzed for at least one of the following properties wavelength, intensity, and Raman shift, most preferably the collected light and/or provided light is analyzed for at least one of the following properties wavelength and intensity.

Applicants disclose the method of Paragraphs 0021 through 0027 wherein the collected light and/or provided light is analyzed using one or more devices selected from the group consisting of a spectrometer, a monochromator, a spectrum analyzer, a photodiode, a photomultiplier tube, an avalanche detector, a camera, a charge coupled device array, a complementary metal oxide semiconductor detector, a photoreceiver, and a polarimeter, preferably the collected light and/or provided light is analyzed using one or more devices selected from the group consisting of a spectrometer, a monochromator, a spectrum analyzer, a photodiode, a photomultiplier tube, an avalanche detector, a camera, a charge coupled device array, a complementary metal oxide semiconductor detector, and a photoreceiver, more preferably the collected light and/or provided light is analyzed using one or more devices selected from the group consisting of a spectrometer, a photodiodes, and a photoreceivers, most preferably the collected light and/or provided light is analyzed using one or more devices selected from the group consisting of a spectrometer and a photodiode.

EXAMPLES

The following examples illustrate particular properties and advantages of some of the embodiments of the present invention. Furthermore, these are examples of reduction to practice of the present invention and confirmation that the principles described in the present invention are therefore valid but should not be construed as in any way limiting the scope of the invention.

Example 1. Real-time Fuel Thermal Stability Test Using Glass Tube Flow

Path. One embodiment of the invention is depicted in FIG. 1, which shows an arrangement in which optical access to the fuel flow was provided using a glass tube to enclose the flowing fuel as it was heated. Fuel was pumped from a supply into the inlet of a glass tube that was contained inside a series of furnaces to control the temperature along the length of the tube. The furnaces were separated by thermal insulators. Optical access to the fuel flow was provided through furnace #2 in this case. The heated fuel exited the outlet of the tube and was routed to a spent fuel dump. The flow rate of the fuel was controlled by the pump and the pressure was controlled by a backpressure regulator. In case of a blockage or malfunction, a bypass valve was provided for safety. As another safety precaution, the heated sections of the tube were contained within an oxygen-free enclosure in case of a fuel leak or a rupture when the furnaces were at a temperature hot enough to ignite the fuel.

Figure 2:
FIG. 2 is a photograph of a glass tube that was used in a test using the embodiment depicted in FIG. 1.

FIG. 2 shows a photograph of a glass tube that was used in a test using the embodiment depicted in FIG. 1. The tube in the photograph was marked with a red pen at intervals of approximately 15 mm. The first 5 segments that are clear and un-darkened correspond to the inlet portion of the tube that the fuel flowed through before entering the vicinity of furnace #1. The next area which is slightly darkened corresponds to furnace #1 which was held at ~400° C. The even darker portions downstream correspond to furnaces #2 (varied from 400-650° C.) and #3 (held at 400° C.), respectively. The total run time of this test was 80 minutes. The final segment on the right of the photo corresponds to the outlet of the glass tube which is downstream of furnace #3. In the areas of the photo that correspond to the vicinity of the furnaces, deposition due to fuel degradation is seen to have visibly darkened the tube. The type and quantity of deposit left in the tube can be characterized by visual inspection, optical spectroscopy, ellipsometry, microscopy, mass spectrometry, or combinations of such measurements.

Figure 3A:
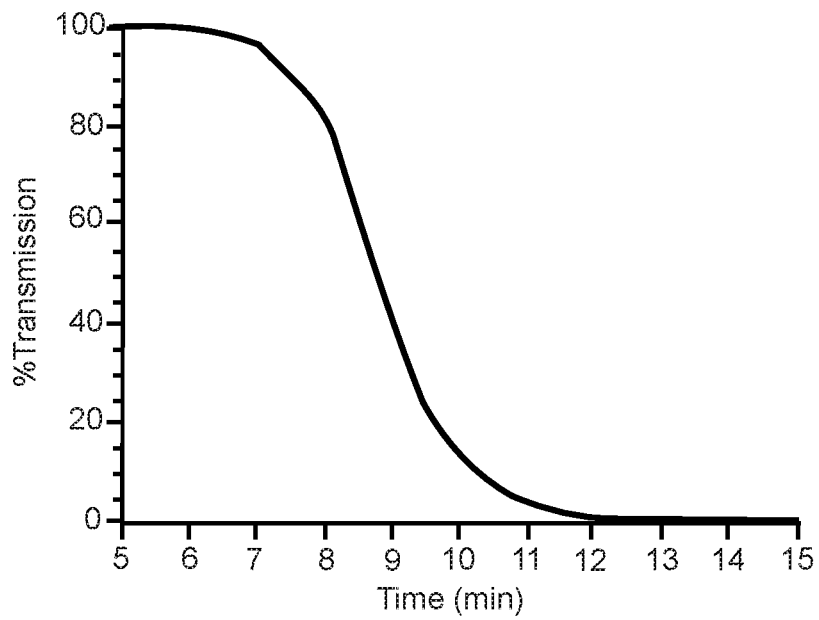
FIG. 3A shows an example of real time data collected using the test method described herein.
Figure 3B:
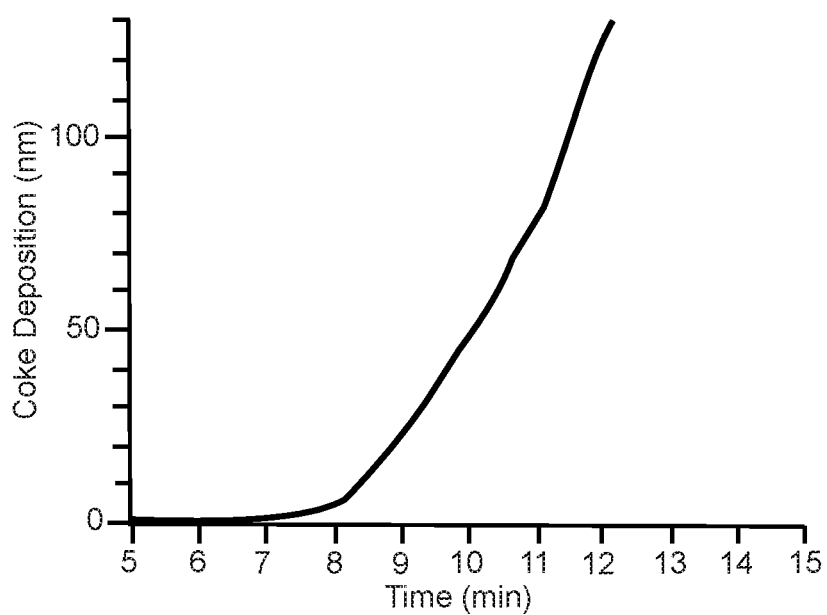
FIG. 3B shows an example of real time data collected using the test method described herein.

FIG. 3 shows an example of real time data collected using the test method described herein. In (a) the % transmission of the tube is shown as measured across the observation ports located in furnace #2 in FIG. 1. At ~7 minutes in the plot, the flow rate of the fuel surrogate (hexanes) was reduced, leading to degradation and deposition. The tube began to darken analogously to the tube in FIG. 2, and the percent transmission was reduced. After several minutes, the tube became opaque such that the percent transmission was ~0%. In (b) we show the calculated thickness of the coke deposition of the tube based upon the drop in percent transmission from (a). The calibration that relates the drop in percent transmission to the thickness of the deposited coke layer was obtained by taking several post-test tubes such as the one photographed in FIG. 2, measuring the percent transmission along the length of the tube, and then breaking the tubes into ~15 mm marked sections. The coke deposit in each section was measured using a carbon burn-off instrument from LECO, Inc. Once the mass of deposit in each section was measured with the LECO instrument, the thickness was then calculated by assuming a coke density of 1.6 grams/cm$^3$, and that the coke was deposited uniformly on the inner surface area of the tube section measured. This calibration was then used to convert percent transmission to coke thickness for each real time measurement. This example demonstrates how having the correct optical access, to include access at temperatures in excess of 400° C., allows the rate of fuel degradation and deposit formation to be determined in real time.

Example 2 High Temperature and Pressure Real-time Fuel Thermal Stability Test Method. A fuel or fuel surrogate is flowed through a heated pathway at a user-controlled pressure and flow rate. The pathway may be heated by single furnace or by a series of furnaces in order to impose a desired thermal history on the fuel flow (e.g. 400° C., then 600° C., then 300° C.). Optical access to the fuel flow is provided at locations chosen along the flow path using optically transparent tubing, windows, or fiber optic ports. The fuel flow is continued for a duration of time during which deposits may be formed if the test temperature exceeds the maximum temperature at which the fuel is thermally stable. Fuel deposits cause the tubing/windows/ports to visually darken as deposits build up. The type and quantity of deposit is examined after the test using visual inspection, optical spectroscopy, ellipsometry, microscopy, mass spectrometry, or combinations of such measurements on the tubing/windows/ports that contain deposits. During the test, the amount and rate of deposition resulting from fuel degradation is measured by using the optical access to the fuel flow to monitor the darkening of the tube as a function of time or temperature.

Every document cited herein, including any cross-referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While the present invention has been illustrated by a description of one or more embodiments thereof and while these embodiments have been described in considerable detail, they are not intended to restrict or in any way limit the scope of the appended claims to such detail. Additional advantages and modifications will readily appear to those skilled in the art. The invention in its broader aspects is therefore not limited to the specific details, representative apparatus and method, and illustrative examples shown and described. Accordingly, departures may be made from such details without departing from the scope of the general inventive concept.

What is claimed is:

1. An apparatus comprising:
a) a chamber, said chamber having an inlet, and an outlet
b) one or more areas of said apparatus providing optical access to said chamber, said one or more areas being configured to deliver and collect light via fiber optics and/or free space couplings;
c) one or more heat sources capable of heating one or more areas of said chamber;
d) one or more devices for providing a pressure differential between said chamber's inlet and said chamber's outlet, said one or more devices being located in communication with said chamber's inlet or said chamber's outlet with the proviso that when said apparatus comprises two or more of said devices, said devices may be located in communication with said chamber's inlet and/or said chamber's outlet;
e) one or more devices for controlling the absolute pressure in said chamber, said one or more devices being located in communication with said chamber's inlet or said chamber's outlet with the proviso that when said apparatus comprises two or more of said devices, said devices may be located in communication with said chamber's inlet and/or said chamber's outlet, said one or more devices when in communication with said chamber's inlet being located before or after said any of said one or more devices for providing a pressure differential between said chamber's inlet and said chamber's outlet that are in communication with said chamber's inlet; preferably said apparatus comprises one device for controlling the absolute pressure in said chamber, said device being located in communication with said chamber's outlet;
f) one or more devices for providing light to said one or more areas of optical access to said chamber;
g) one or more devices for collecting light from said one or more areas of optical access to said chamber;
h) one or more devices for measuring one or more properties of said collected light and optionally one or more devices for one or more properties of said provided light and/or one or more devices for measuring one or more properties of said collected light and optionally one or more properties of said provided light; and i) optionally, one or more optical filters for filtering light, said one or more optical filters for filtering light being placed before and/or incorporated into said one or more devices for providing light to said one or more areas of optical access to said chamber, before and/or incorporated into said one or more devices for collecting light from said one or more areas of optical access to said chamber and/or before and/or incorporated into said one or more devices for measuring one or more properties of said collected light and optionally one or more properties of said provided light.

2. The apparatus of claim 1 comprising one device providing a pressure differential between said chamber's inlet and said chamber's outlet, said device being located in communication with said chamber's inlet.

3. The apparatus of claim 1 wherein:
a) said chamber has a symmetric shape or an asymmetric shape;
b) said apparatus comprises three or more heat sources capable of heating three or more areas of said chamber;
c) said apparatus comprises two or more areas of optical access to said chamber;
d) said one or more devices for providing a pressure differential between said chamber's inlet and said chamber's outlet comprises a pump and/or pressurized vessel providing a pressure differential between said chamber's inlet and said chamber's outlet;
e) said one or more devices for controlling the absolute pressure in said chamber comprises one or more pressure or flow regulator devices located either upstream or downstream of said at least one heat source;
f) each of said one or more devices for providing light to said one or more areas of optical access to said chamber is independently a laser, a lamp, a light emitting diode or a glow bar;
g) each of said one or more devices for collecting light from said one or more areas of optical access to said chamber comprises a fiber optic device or a free space coupled device;
h) each of said one or more devices for measuring one or more properties of said collected light and optionally one or more properties of said provided light is independently a spectrometer, a monochromator, a spectrum analyzer, a photodiode, a photomultiplier tube, an avalanche detector, a camera, a charge coupled device array, a complementary metal oxide semiconductor detector, a photoreceiver, or a polarimeter.

4. The apparatus of claim 3 wherein:
a) said chamber is cylindrical or rectangular, most preferably said chamber is cylindrical;
b) said apparatus comprises three or more heat sources capable of isothermally heating three or more areas of said chamber, more preferably said apparatus comprises three or more heat sources capable of isothermally heating three or more areas of said chamber with thermal insulation between each isothermal heated zone;
c) said apparatus comprises three or more areas of optical access to said chamber for each of said at least one heat source;
d) said one or more devices for providing a pressure differential between said chamber's inlet and said chamber's outlet comprises a pump providing a pressure differential between said chamber's inlet and said chamber's outlet;
e) said one or more devices for controlling the absolute pressure in said chamber comprises a backpressure regulator located downstream of said at least one heat source;
f) each of said one or more devices for providing light to said one or more areas of optical access to said chamber is independently a laser or a light emitting diode having an emission spectrum of from about 1.99 nm to about 0.01 nm in breadth;
g) each of said one or more devices for collecting light from said one or more areas of optical access to said chamber comprises a fiber optic device having temperature tolerance above about 700° C. to about 1700° C.;
h) each of said one or more devices for measuring one or more properties of said collected light and optionally one or more properties of said provided light is independently a spectrometer or a photodiode.

5. The apparatus of claim 1 wherein:
a) said chamber comprises a material selected from the group coinciding of steel, iron, brass, bronze, copper, titanium, tantalum, nickel, tungsten, silver, gold, platinum, aluminum, glass, quartz, sapphire, silicon dioxide, diamond, rubber, plastic, graphite and mixtures thereof;
b) each of said one or more areas of said apparatus providing optical access to said chamber independently comprising a material selected from the group consisting of glass, quartz, sapphire, silicon dioxide, diamond, zirconium fluoride, indium fluoride, magnesium fluoride, calcium fluoride, silicon, barium fluoride, zinc selenide, germanium, zinc sulfide, and mixtures thereof; and
c) each of said heat sources capable of heating one or more areas of said chamber is independently selected from the group consisting of resistive heaters, laser heating, electron beam heating, convective ovens, and radiative heaters.

6. The apparatus of claim 5 wherein:
a) said chamber comprises a material selected from the group coinciding of steel, quartz, graphite and mixtures thereof,
b) each of said one or more areas of said apparatus providing optical access to said chamber comprising a material selected from the group consisting of glass, quartz, silicon dioxide, zirconium fluoride, indium fluoride, magnesium fluoride, calcium fluoride, silicon, barium fluoride, zinc selenide, and mixtures thereof said materials; and
c) each of said heat sources capable of heating one or more areas of said chamber is independently selected from the group consisting of resistive heaters.

7. The apparatus of claim 1 wherein at least one of said devices for measuring one or more properties of said collected light measures one or more properties of said provided light.

8. A method of determining the thermal stability of a hydrocarbon, said method comprising passing said hydrocarbon through the apparatus of claim 1.

9. The method of claim 8 wherein said fuel is said fuel is a rocket, jet, or missile fuel.

10. The method of claim 8 wherein said fuel, is selected from the group consisting of JP7, JP10, JP8, JP5, JetA, JetA1, F24, RP2 and mixtures thereof.

11. The method of claim 8 wherein:
a) said hydrocarbon is heated while in said apparatus's chamber to a temperature of from about 150° C. to 750° C. about;
b) said hydrocarbon having a residence time in said chamber from about 0.1 seconds to about 300 seconds;
c) the absolute pressure in said chamber is from about 1 atm to about 200 atm;
d) light is provided to one or more areas of optical access to said chamber;
e) light is collected from said one or more areas of optical access to said chamber; and
f) said collected light is measured, and said provided light is optionally measured.

12. The method of claim 8 wherein:
a) said hydrocarbon is heated while in said apparatus's chamber to a temperature of from about 500° C. to 750° C. about; and said hydrocarbon is heated at a rate of from about 2.5° C./sec to about 7500° C./sec;
b) said hydrocarbon having a residence time in said chamber from about 0.1 seconds to about 10 seconds;
c) the absolute pressure in said chamber is from about 25 atm to about 150 atm;
d) light is provided to one or more areas of optical access to said chamber;
e) light is collected from said one or more areas of optical access to said chamber; and
f) said collected light is measured, and said provided light is measured prior to being provided.

13. The method of claim 8 wherein said provided light is measured.

14. The method of claim 8 wherein:
a) said provided light has a wavelength of from about 180 nm to about 20 µm; and/or
b) said collected light has a wavelength of from about 180 nm to about 20 µm and the wavelength of said provided light is filtered out of said collected light.

15. The method of claim 14 wherein said collected light has a wavelength of from about 180 nm to about 20 µm, said provided light has a wavelength of from about 400 nm to about 600 nm; and the wavelength of said provided light is filtered out of said collected light.

16. The method of claim 8 wherein said method comprises one, two, three or four of the following steps:
a) said provided light is provided by a laser, a lamp, a light emitting diode, and/or a glow bar;
b) said provided light is measured by a spectrometer, a monochromator, a spectrum analyzer, a photodiode, a photomultiplier tube, an avalanche detector, a camera, a charge coupled device array, a complementary metal oxide semiconductor detector, a photoreceiver, and/or a polarimeter;
c) said collected light is collected by a fiber optic device and/or free space coupled device;
d) said collected light is measured by a spectrometer, a monochromator, spectrum analyzer, a photodiode, a photomultiplier tube, an avalanche detector, a camera, a charge coupled device array, a complementary metal oxide semiconductor detector, a photoreceiver, and/or a polarimeter.

17. The method of claim 16 wherein said method comprises one, two, three or four of the following steps:
a) said provided light is provided by a laser and/or a light emitting diode, said light emitting diode having an emission spectrum from about 1.99 nm to about 0.01 nm in breath;
b) said provided light is measured by a photodiode and/or a photoreceiver;
c) said collected light is collected by a fiber optic devices having temperature tolerance above about 700° C. to about 1700° C.;
d) said collected light is measured by a spectrometer and/or a photodiode.

18. The method of claim 8 wherein the collected light and/or provided light is analyzed for at least one of the following properties wavelength, intensity, Raman shift, polarity, and phase.

19. The method of claim 18 wherein the collected light and/or provided light is analyzed for at least one of the following properties: wavelength and intensity.

20. The method of claim 8 wherein the collected light and/or provided light is analyzed using one or more devices selected from the group consisting of a spectrometer, a monochromator, a spectrum analyzer, a photodiode, a photomultiplier tube, an avalanche detector, a camera, a charge coupled device array, a complementary metal oxide semiconductor detector, a photoreceiver, and a polarimeter.

21. The method of claim 20 wherein the collected light and/or provided light is analyzed using one or more devices selected from the group consisting of a spectrometer and a photodiode.

* * * * *